(12) United States Patent
Wolf et al.

(10) Patent No.: US 7,422,763 B2
(45) Date of Patent: *Sep. 9, 2008

(54) ACID CONTROLLED INDUCED VISCOSITY FIBER SYSTEM AND USES THEREOF

(75) Inventors: Bryan W. Wolf, Johnstown, OH (US); Bruce B. Blidner, Westerville, OH (US); Keith A. Garleb, Pickerington, OH (US); Chron-Si Lai, Blacklick, OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/157,296

(22) Filed: May 29, 2002

(65) Prior Publication Data

US 2002/0193344 A1   Dec. 19, 2002

Related U.S. Application Data

(60) Provisional application No. 60/294,817, filed on May 31, 2001.

(51) Int. Cl.
| A61K 31/723 | (2006.01) |
|---|---|
| A61K 31/731 | (2006.01) |
| A61K 31/732 | (2006.01) |
| A61K 31/734 | (2006.01) |
| A61K 31/736 | (2006.01) |
| A23L 1/0524 | (2006.01) |

(52) U.S. Cl. .................... 426/573; 426/577; 426/590; 426/658; 514/54; 514/866; 514/909; 514/911

(58) Field of Classification Search .................. 514/54; 424/439, 488, 499
See application file for complete search history.

(56) References Cited

U.S. PATENT DOCUMENTS

| 4,701,329 A * | 10/1987 | Nelson et al. ................. 426/74 |
|---|---|---|
| 4,921,877 A | 5/1990 | Cashmere et al. ........... 514/866 |
| 4,959,227 A * | 9/1990 | Amer .......................... 426/35 |
| 5,034,378 A * | 7/1991 | Cox ............................ 514/23 |
| 5,085,883 A | 2/1992 | Garleb et al. ............... 426/590 |
| 5,104,677 A | 4/1992 | Behr et al. .................. 426/590 |
| 5,292,723 A | 3/1994 | Audry et al. .................. 514/58 |
| 5,324,526 A * | 6/1994 | Iwata et al. .................... 426/2 |
| 5,470,839 A | 11/1995 | Laughlin et al. ............. 514/53 |
| 5,700,782 A * | 12/1997 | Cope et al. ................... 514/21 |
| 5,776,887 A | 7/1998 | Wibert et al. .................. 514/2 |
| 6,020,017 A | 2/2000 | Mingione ................... 426/590 |
| 6,221,836 B1 | 4/2001 | Beale et al. .................... 514/2 |
| 6,248,375 B1 * | 6/2001 | Gilles et al. ................. 426/72 |
| 6,429,190 B1 | 8/2002 | Portman ........................ 514/2 |

FOREIGN PATENT DOCUMENTS

| EP | 0768043 A2 | 10/1996 |
|---|---|---|
| JP | 03-290157 | * 12/1991 |
| WO | WO 96/25054 | 8/1996 |

OTHER PUBLICATIONS

Ohta, A.; Taguchi, A. Takizawa, T.; Adachi, T.; Kimura, S.; Hashizume, N. International Journal for Vitamin and Nutrition Research (1997), 67(1), 55-61.*

JAPIO abstract AN 1991-290157 for JP 03-290157, 12-1991.*
"Milk Notes" url = http://www.sciencebyjones.com/PDF%20files/milk%20Note1.pdf Accessed from the Web Jul. 21, 2005.*
Murray, S. et al "Apparent digestibility and glycaemic responses . . . " Food Chem. Toxicol. (1999) vol. 37, pp. 47-56.*
Wang, Z. et al "Sol-Gel transition of alginate solution by the addition ov various divalent cations . . . " Biopolymers (1994) vol. 34, pp. 737-746.*
Slim-Fast®, http://www.slim-fast.com/products/lactose.asp, Jun. 2001.
Glytrol, 1995 Clintec Nutrition Company.
Compelling Comparisons Glucerna® , Mar. 1996, Ross Products Division, Abbott Laboratories.
PediaSure®, Mar. 2001, Pediatric Nutritionals Product Guide, Ross Products Division, Abbott Laboratories.
Ensure®, Ross Products Division, Abbott Laboratories, dates not available.
Glucerna®, Ross Products Division, Abbott Laboratories, dates not available.
Glucerna® Shake, Ross Products Division, Abbott Laboratories, dates not available.
Choice$dm$™, 1997 Mead Johnson & Company.
Resource® Diabetic, 1995 Clinical Products Division, Sandoz Nutrition Corporation.
Compelling Comparisons Glucerna®, 1996 Ross Products Division, Abbott Laboratories.
Brutomesso, D,; Briani, G,; Bilardo, G,; Vitale, E.; Lavagnini, T,; Marescotti, C,; Duner, E,; Giorato, C,; Tiengo, A, The medium-term effect of natural or extractive dietary fibres on plasma amino acids and lipids in type 1 diabetics.*Diabetes Research and Clinical Practice.* 1989, 6, 149-155.
Krotkeiewski, M., Effect of Guar Gum on BodyWeight, Hunger Ratings and Metabolism in Obese Subjects. *Br. J. Nutr*, 1984, 52, 97-105.
Multivalent cations, The Merck Index, 10$^{th}$ edition, 1983.
"Fermentability of Various Fiber Sources by Human Fecal Bacteria In Vitro", American Journal Clinical Nutrition, 1991; 53: 14181424.
Jevity® Plus, Ross Products Division, Abbott Laboratories, date not available.

* cited by examiner

*Primary Examiner*—Leigh C Maier
(74) *Attorney, Agent, or Firm*—William J. Winter; Sandra E. Weida

(57) ABSTRACT

The present invention relates generally to a method of blunting the postprandial glycemic response to a meal by feeding an acid controlled induced viscosity fiber system. The first component of the induced viscosity fiber system is anionic soluble fiber. The second component of the induced viscosity fiber system is water-insoluble, acid-soluble multivalent cations. The fiber system will typically be incorporated into a meal replacement nutritional.

The present invention also refers to a method of delivering soluble fiber to diabetics and to persons needing to lose weight. Additionally, the invention refers to a method of promoting the feeling of fullness and satiety by feeding a nutritional product containing the induced viscosity fiber system.

12 Claims, 7 Drawing Sheets

ACID CONTROLLED INDUCED VISCOSITY FIBER SYSTEM AND USES THEREOF

CROSS REFERENCE

This application is a continuation-in-part of U.S. Patent Application Ser. No. 60/294,817, which was filed on May 31, 2001. This application is related to the Polymer Controlled Induced Viscosity Fiber System and Uses Thereof Ser. No. 10/157,297 and Dual Induced Viscosity Fiber System and Uses Thereof Ser. No. 10/157,298 continuation-in-part applications, filed concurrently herewith by Wolf, the contents of which are herein incorporated by reference.

TECHNICAL FIELD

The present invention relates generally to a method of blunting the postprandial glycemic response to a meal. The invention also relates to an induced viscosity fiber system and the liquid products that incorporate the induced viscosity fiber system. Further, the invention relates to a method of incorporating soluble fiber into a liquid product without the typical negative organoleptic or physical stability issues. The invention also relates to a method of inducing the feeling of fullness and satiety by feeding the induced viscosity fiber system.

BACKGROUND OF THE INVENTION

Diabetes is the seventh leading cause of death in the United States and the sixth leading cause of death by disease among Americans. It is estimated that 15.7 million people, or 7.8% of the U.S. population, suffer from diabetes. Consequently, the economic burden of diabetes is great, with an estimated total annual economic cost of $98 billion in 1997. This includes $44 billion for direct medical and treatment costs, and $54 billion for indirect costs due to disability and mortality.

The cause of diabetes is unknown, however, known risk factors for this disease are multi-factorial. Genetics and environmental factors such as obesity and sedentary lifestyle appear to contribute to diabetes incidence. Type 2 diabetes, a disorder resulting from the body's inability to make enough or properly use insulin, accounts for 90 to 95 percent of all diabetes. This type of diabetes is reaching epidemic proportions in America because of the increasing age of the population, in addition to a greater prevalence of obesity and sedentary lifestyles.

Standard treatment of diabetes involves maintenance of as near-normal blood glucose levels as possible by balancing food intake with insulin or oral glucose-lowering medications and physical activity levels. Low calorie diets and weight loss usually improve short-term glycemic levels and have the potential to improve long-term metabolic control. However, traditional dietary strategies, and even very-low-calorie diets, have usually not been effective in achieving long-term weight loss.

Obesity is associated with numerous chronic diseases, such as type 2 diabetes, heart disease, hypertension, stroke, dyslipidemia, osteoarthritis, sleep apnea, gallbladder disorders, respiratory problems, and malignancy. A loss of only 5% to 10% of baseline weight in an obese patient with type 2 diabetes, hypertension, or dyslipidemia can improve glycemic control, decrease blood pressure, and improve the lipid profile, respectively. Lifestyle modification by changes in diet or increase in exercise is usually the first step in treating overweight or obese persons. However, behavioral modification is often not very successful, and long-term maintenance of diet or exercise changes is attained by less than 15% of persons who initiate these changes. In addition, restricted calorie diets cannot be continued over a long period of time, and the majority of the weight lost on these diets is re-gained.

One approach to initiating and maintaining weight loss in overweight individuals is by inducing satiation (feeling of fullness during a meal) and satiety (feeling of fullness after a meal). Various gastrointestinal mechanisms trigger both the initiation and termination of eating in individual persons. Although gastric distention is a normal sign of "fullness" and plays a role in controlling food intake, its effects are temporary and distinct from feelings of satiety associated with a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.

The concept that dietary fiber may aid in the treatment of hyperglycemia has been suggested since the 1970's. Viscous soluble fiber (e.g., guar gum, psyllium, oat β-glucan) supplementation to test meals has been shown to effectively blunt postprandial glycemia. Despite the existence of some in vivo evidence; however, there is still considerable doubt about the efficacy of dietary fiber in the treatment of hyperglycemia. This doubt may exist because different types of dietary fibers have different physiological effects. As analytical methods for dietary fiber improve, so does our understanding of physiological fiber effects. For example, soluble viscous fibers generally have a greater effect on carbohydrate metabolism in the small intestine by slowing the rate of absorption, although delayed gastric emptying also may play a role. These phenomena should decrease the rate at which glucose enters the systemic circulation and delay the postprandial rise in blood glucose. While the applicability of this concept is evident, its clinical use is limited. Unfortunately, foodstuffs containing viscous fibers (e.g., guar gum) usually exhibit slimy mouthfeel, tooth packing, and poor palatability. The overall hedonic quality of guar-containing foods can be improved by reducing the average molecular weight (e.g., through chemical hydrolysis) of the galactomannan in guar gum; however, this results in a concurrent loss in clinical efficacy.

Products designed as sole source of nutrition and as nutritional supplements for the person with diabetes are commercially available. The commercial products are typically liquid and include higher amounts of fat. The higher fat is desired in a liquid nutritional as the fat slows down stomach emptying, thereby delaying the delivery of nutrients to the small intestine, which blunts the absorption curve of carbohydrates after a meal.

Glucerna® (Ross Products Division of Abbott Laboratories, Columbus Ohio) is a liquid nutritional with fiber for patients with abnormal glucose tolerance. Sodium and calcium caseinates make up 16.7% of total calories as protein; maltodextrin, soy polysaccharide and fructose make up 34.3% of total calories as carbohydrate; and high oleic safflower oil and canola oil make up 49% of total calories as fat. Soy polysaccharide contributes 14.1 g/1000 ml of total dietary fiber. The RDI for vitamins and minerals is delivered in 1422 kcals. The product also contains the ultra trace minerals selenium, chromium and molybdenum and the conditionally essential nutrients carnitine and taurine.

Choice dm® (Mead Johnson & Company, Evensville, Ind.) is a nutritionally complete beverage for persons with glucose intolerance. Milk protein concentrate makes up 17% of total calories as protein; maltodextrin and sucrose make up 40% of total calories as carbohydrate; and high oleic sunflower oil and canola oil make up 43% of total calories as fat. Microcrystalline cellulose, soy fiber and gum acacia contribute 14.4 g/1000 ml of total dietary fiber. The RDI for vitamins and minerals is delivered in 1060 kcals. The product also contains the ultra trace minerals selenium, chromium and molybdenum and the conditionally essential nutrients, carnitine and taurine.

Resource® Diabetic (Sandoz Nutrition Corporation, Berne, Switzerland) is a complete liquid formula with fiber specifically designed for persons with type 1 and type 2 diabetes and for persons with stress-induced hyperglycemia. Sodium and calcium caseinates, and soy protein isolate make up 24% of total calories as protein; hydrolyzed corn starch and fructose make up 36% of total calories as carbohydrate; and high oleic sunflower oil and soybean oil make up 40% of total calories as fat. Partially hydrolyzed guar gum contributes 3.0 g/8 fl. oz. of total dietary fiber. The RDI for vitamins and minerals is delivered in 2000 kcals. The product also contains the ultra trace minerals selenium, chromium and molybdenum and the conditionally essential nutrients carnitine and taurine.

Ensure® Glucerna® Shake (Ross Products Division of Abbott Laboratories, Columbus Ohio) is an oral supplement specifically designed for people with diabetes. Sodium and calcium caseinates and soy protein isolate make up 18% of total calories as protein; maltodextrin, fructose, maltitol, soy polysaccharide and FOS make up 47% of total calories as carbohydrate; and high oleic safflower oil and canola oil make up 35% of total calories as fat. Soy polysaccharide and fructooligosaccharides (FOS) contribute 3.0 g/8 fl. oz. of total dietary fiber. At least 25% of the DV for 24 key vitamins and minerals are delivered in 8 fl. oz. The product also contains the ultra trace minerals selenium, chromium and molybdenum.

U.S. Pat. No. 4,921,877 to Cashmere et al. describes a nutritionally complete liquid formula with 20 to 37% of total caloric value from a carbohydrate blend which consists of corn starch, fructose and soy polysaccharide; 40 to 60% of total caloric value from a fat blend with less than 10% of total calories derived from saturated fatty acids, up to 10% of total calories from polyunsaturated fatty acids and the balance of fat calories from monounsaturated fatty acids; 8 to 25% of total caloric value is protein; at least the minimum U.S. RDA for vitamins and minerals; effective amounts of ultra trace minerals chromium, selenium and molybdenum; and effective amounts of carnitine, taurine and inositol for the dietary management of persons with glucose intolerance.

U.S. Pat. No. 5,776,887 to Wibert et al. describes a nutritional composition for the dietary management of diabetics containing a 1 to 50% total calories protein; 0 to 45% total calories fat, 5 to 90% total calories carbohydrate system and fiber. The carbohydrate system requires a rapidly absorbed fraction such as glucose or sucrose, a moderately absorbed fraction such as certain cooked starches or fructose and a slowly absorbed fraction such as raw cornstarch.

U.S. Pat. No. 5,292,723 to Audry et al. describes a liquid nutritional composition containing a lipid fraction, a protein fraction and a specific combination of glucides useful as dietetics. The glucide fraction consists of glucose polymers and slowly absorbed glucides.

U.S. Pat. No. 5,470,839 to Laughlin et al. describes a composition and method for providing nutrition to a diabetic patient. The low carbohydrate, high fat enteral composition contains a protein source, a carbohydrate source including a slowly digested high amylose starch and soluble dietary fiber, and a fat source that includes a high percentage of monounsaturated fats.

U.S. Pat. No. 5,085,883 to Garleb et al. describes a blend of dietary fiber which includes by weight: 5% to 50% of a dietary fiber which is both soluble and fermentable; 5% to 20% of a dietary fiber which is both soluble and non-fermentable; and 45% to 80% of a dietary fiber which is both insoluble and non-fermentable. Preferably, the dietary fiber, which is both soluble and fermentable, is gum arabic; the dietary fiber, which is both soluble and non-fermentable, is sodium carboxymethylcellulose; and the dietary fiber, which is both insoluble and non-fermentable, is oat hull fiber.

U.S. Pat. No. 5,104,677 to Behr et al. describes a liquid nutritional product that contains a fat source and a dietary fiber system. The dietary fiber system as a whole includes by weight: (a) 5% to 50% dietary fiber which is both soluble and fermentable, 5% to 20% dietary fiber which is both soluble and non-fermentable, and 45% to 80% dietary fiber which is both insoluble and non-fermentable. Less than 10% of the total calories in the product comprise saturated fatty acids, no more than 10% of the total calories in the product is polyunsaturated fatty acids, and the ratio of the n-6 to n-3 fatty acids in the product being in the range of 2 to 10. Preferably the dietary fiber that is both soluble and fermentable, is gum arabic; the fiber that is both soluble and non-fermentable, is sodium carboxymethylcellulose, and the fiber that is both insoluble and non-fermentable, is oat hull fiber.

The prior art describes multi-component carbohydrate systems that blunt the glycemic response by requiring sources of carbohydrate that are absorbed at different rates. These multi-component carbohydrate systems possess physical characteristics that make incorporation of the carbohydrate systems into nutritional formulas difficult. Additionally, these multi-component carbohydrate systems are often found to possess unacceptable organoleptic characteristics. For example, guar gum functions to provide viscosity in the stomach, thereby slowing the release of nutrients to the small intestine. Unfortunately, foodstuffs containing guar gum typically exhibit slimy mouth-feel, tooth packing, and poor palatability. Additionally, effective amounts of guar gum increase the viscosity of liquid products such that the liquid product gels in the container. The overall hedonic quality of guar-containing foods can be improved by reducing the average molecular weight (i.e., through hydrolysis) of the galactomannan in guar gum; however, this results in a concurrent loss in clinical efficacy. In addition to the challenge of making a palatable product, dietary supplementation with effective levels of guar gum is also associated with gastrointestinal side effects (e.g., flatulence and diarrhea) from its colonic fermentation, because guar gum is a rapidly fermented carbohydrate.

Furthermore, adding a high level of soluble fiber destabilizes nutritional products. This instability can be seen as an increase in product grain scores or in phase separation upon heat treatment. It is not known why soluble fiber destabilizes ready-to-feed (RTF) products. The literature suggests that anionic fiber interacts with protein and the resultant fiber-protein complex may be insoluble under certain conditions, causing high grain scores. Another possibility is that, in general, polymers, such as fiber and protein, are not spatially compatible. Above a certain concentration, these polymers will separate into two distinct phases, one rich in polysaccharide and another rich in protein. Addition of soluble fiber could also cause phase separation due to a concept known as depletion flocculation. Depletion flocculation would yield a fat rich phase and relatively fat poor phase. Decreasing the level of soluble protein, optimizing the protein type, or carefully selecting fiber sources could improve product stability.

Thus, a need has developed in the art for a fiber system which acts to blunt the absorption curve of carbohydrates after a meal, while being well tolerated, organoleptically acceptable and easily incorporated into nutritional matrixes.

The disease state of many diabetics is complicated by their overweight status. As described above, the increased viscosity in the stomach results in the slow release of nutrients to the small intestine. This slow release also induces the feeling of fullness and satiety after a meal. For example, 9 to 20 gm/day of supplemental guar gum for 4 to 8 weeks has been shown to significantly reduce body weight and sensations of hunger compared to control. (Bruttomesso, D.; Briani, G.; Bilardo, G.; Vitale, E.; Lavagnini, T.; Marescotti, C.; Duner, E.; Giorato, C.; Tiengo, A. The medium-term effect of natural or extractive dietary fibres on plasma amino acids and lipids in type 1 diabetics. *Diabetes Research and Clinical Practice.* 1989, 6, 149-155; Krotkiewski, M. Effect of guar gum on body-weight, hunger ratings and metabolism in obese subjects. *Br. J. Nutr.* 1984, 52, 97-105.) However, the same issues described above in tolerance and product development apply to the use of soluble fiber to induce the feeling of fullness and satiety. The commercial market responded with guar gum capsules that addressed the product stability and mouth feel issues described above. However, safety issues developed when the capsules were found to swell in the throat increasing the risk of chocking. The guar gum capsules have since been removed from the market.

Thus, a need has developed in the weight loss art for a fiber system that induces the feeling of fullness and satiety, while being well tolerated, organoleptically acceptable and easily incorporated into nutritional matrixes.

SUMMARY OF THE INVENTION

The inventors have discovered a novel fiber system that allows incorporation of soluble, viscous fibers into stable liquid products. These nutritional products are clinically effective in blunting the glycemic response to a meal while addressing the negative organoleptic, tolerance and physical stability issues associated with soluble viscous fibers. This novel system will be referred to as the induced viscosity fiber system. It is based upon building viscosity in vivo by the indirect action of acid. The induced viscosity fiber system utilizes anionic soluble dietary fibers that do not form highly viscous solutions at relatively modest concentrations and contain high levels of uronic acid groups. These groups react with positively charged salts to cross link individual fiber molecules, producing a highly viscous solution (or gel at high fiber concentrations). Using this induced viscosity fiber system, a liquid product can be formulated that is not viscous at neutral pH but becomes viscous upon acidification. For example, when the hydrochloric acid in the gastric chyme reacts with water insoluble calcium salts to produce ionized calcium, the resultant free calcium ion cross-link with uronic acid groups within the anionic polymer and increases the viscosity of the chyme. A product formulated with the proper type of fiber and a water-insoluble, acid-soluble cation source has a low viscosity at a neutral pH, is drinkable, and becomes highly viscous following ingestion. The inventors discovered that the acid controlled induced viscosity fiber system produces the same glycemic response as a nutritional product specifically designed for the nutritional support of a diabetic. Further, the induced viscosity fiber system uses soluble fiber that is less fermentable and less viscous than the prior art, thereby minimizing the tolerance and product development issues typically associated with soluble fermentable fiber. As discussed above, this induced fiber system of the instant invention would be applicable to people with diabetes, for people with insulin resistance as well as a preventative therapy for high-risk populations (e.g., obese and first degree relatives of people with type 2 diabetes mellitus) and for those individuals needing to lose weight.

The first embodiment of the present invention refers to a nutritional product comprising the acid controlled induced viscosity fiber system. The first component of the induced viscosity fiber system is anionic soluble fiber. The second component of the induced viscosity fiber system is water-insoluble, acid-soluble multivalent cations. The fiber system will typically be incorporated into a meal replacement nutritional.

The present invention also refers to a method of delivering soluble fiber to diabetics and to persons needing to lose weight. The present invention also refers to a method of blunting the postprandial glycemic response of a human by feeding a liquid nutritional product containing the induced viscosity fiber system. Additionally, the invention refers to a method of promoting the feeling of fullness and satiety by feeding a nutritional product containing the induced viscosity fiber system.

DETAILED DESCRIPTION OF THE INVENTION

As used in this application:
a. "glycemic index" (GI) is calculated by dividing the blood glucose incremental area under the curve (AUC) of the test food by the blood glucose AUC of the reference food and multiplying by 100, where the available carbohydrate content of test and reference foods are the same. The reference food is typically glucose or white bread, which has the standard GI of 100.
b. "anionic soluble fiber" refers to water-soluble fibers that carry negative charges after being dissolved in water.
c. "water-insoluble, acid-soluble multivalent cations" refers to salts that are not soluble in water at neutral pH and will react with acid releasing the cation. Multivalent cations listed in The Merck Index, Tenth Edition as insoluble or practically insoluble in water and soluble in acid are examples of suitable salts.
d. "satiation" refers to the feeling of fullness during a meal. Various gastrointestinal mechanisms trigger the termination of eating in individuals. Although gastric distention is a normal sign of "fullness" and plays a role in controlling food intake, its effects are temporary and distinct from feelings of satiety associated with a meal.

e. "satiety" refers to the feeling of fullness after a meal. Satiety is associated with postprandial sensations related to the activation of intestinal chemoreceptors, such as cholecystokinin, leptin, insulin, hypothalamic neuropeptide Y, and glucocorticoid hormones. These postprandial sensations, which are largely responsible for the phenomenon of satiation after a meal is consumed, have a longer-lasting effect on satiety or hunger than gastric distention.

f. The term "acid requirement" refers to the amount of acid required to ionize the multivalent cation that then cross-links the anionic soluble fiber molecules thereby developing a viscous digesta.

g. the term "dextrose equivalence" (DE) refers to a quantitative measure of the degree of starch polymer hydrolysis. It is a measure of reducing power compared to a dextrose (glucose) standard of 100. The higher the DE, the greater the extent of starch hydrolysis. As the starch is further hydrolyzed (higher DE), the average molecular weight decreases and the carbohydrate profile changes accordingly. Maltodextrins have a DE less than 20. Corn syrup solids have a DE of 20 or higher and are more rapidly absorbed.

h. "soluble" and "insoluble" dietary fiber is determined using American Association of Cereal Chemists (AACC) Method 32-07. A "soluble" dietary fiber source refers to a fiber source in which at least 60% of the dietary fiber is soluble dietary fiber as determined by AACC Method 32-07, and an "insoluble" dietary fiber source refers to a fiber source in which at least 60% of the total dietary fiber is insoluble dietary fiber as determined by AACC Method 32-07.

i. "fermentable" and "non-fermentable" dietary fiber is determined by the procedure described in "Fermentability of Various Fiber Sources by Human Fecal Bacteria In Vitro", at AMERICAN JOURNAL CLINICAL NUTRITION, 1991; 53:1418-1424. This procedure is also described in U.S. Pat. No. 5,085,883 to Garleb et al. "Non-fermentable" dietary fiber refers to dietary fibers that have a relatively low fermentability of less than 40% by weight, preferably less than 30% by weight, and the term "fermentable" dietary fiber refers to dietary fibers which have a relatively high fermentability of greater than 60% by weight, preferably greater than 70% by weight.

j. the term "total calories" refers to the total caloric content of a definitive weight of the finished nutritional product.

k. the term "Reference Daily Intakes or RDI" refers to a set of dietary references based on the Recommended Dietary Allowances for essential vitamins and minerals. The Recommended Dietary Allowances are a set of estimated nutrient allowances established by the National Academy of Sciences, which are updated periodically to reflect current scientific knowledge.

l. the term "in vivo viscosity" refers to the maximum viscosity measured after the samples have been titrated with 0.1N HCl. Aliquots of 0.1N HCl were added to 250 gm of the acid controlled induced viscosity fiber system followed by shearing using a Glass-Col mixer for 30 minutes. The viscosity following shearing is measured using a Brookfield (model DVII+) viscometer with a 62 spindle at room temperature. The induced viscosity of nutritional products that contain the induced viscosity fiber system is measured after the addition of 0.1N HCl to 250 gm of the nutritional product followed by shearing using a Glass-Col mixer for 30 minutes. The viscosity following shearing is measured using a Brookfield (model DVII+) viscometer with a 62 spindle at room temperature.

m. the term "viscosity" is the ratio of shear stress to shear rate, expressed as dynes-second/cm$^2$, or poise. A centipoise (cps) is one hundredth of a poise. A poise is a unit of coefficient of viscosity, defined as the tangential force per unit area required to maintain one unit difference in velocity between two parallel planes separated by one centimeter of fluid. Any viscosity determination should be carried out using a Brookfield (model DVII+) viscometer with a 62 spindle at room temperature. The viscosity is measured by operating the viscometer at a spindle speed that is the highest speed possible to obtain a reading that is on scale.

n. any reference to a numerical range in this application should be construed as an express disclosure of every number specifically contained within that range and of every subset of numbers contained within that range. Further, this range should be construed as providing support for a claim directed to any number, or subset of numbers in that range. For example, a disclosure of 1-10 should be construed as supporting a range of 2-8, 3-7, 5, 6, 1-9, 3.6-4.6, 3.5-9.9, 1.1-9.9, etc.

o. the terms "induced viscosity fiber system", "acid controlled induced viscosity fiber system", "acid induced viscosity fiber system", "acid induced viscosity system" and "induced viscosity system" are used interchangeably and refer to the instant invention.

The acid induced viscosity fiber system of the instant invention functions due to the type of soluble fiber utilized. Soluble fibers containing high levels of carboxylic acid groups react with multivalent cations resulting in increased viscosity. Such fibers with relatively low viscosity at neutral pH can develop viscosities to over 10,000 cps upon acidification. This increase in viscosity is a result of the ionization of, for example, calcium and the subsequent cross-linking of, for example, alginate.

For maximum clinical impact, typically, the induced viscosity fiber system will be incorporated into meal replacement beverages such as Glucerna®, Ensure®, Choice DM®, Slim Fast®, Pediasure®, Glytrol®, Resource® Diabetic, etc. Methods for producing such food products are well known to those skilled in the art. The following discussion is intended to illustrate such diabetic and weight loss meal replacement products and their preparation.

The nutritional formulas of this invention are designed to be used as a meal replacement or as a supplement. Because the product can be used as a meal replacement it will contain a protein source, a lipid source, a carbohydrate source, and vitamins, and minerals. Such amounts are well known by those skilled in the art and can be readily calculated when preparing such products. While these meal replacement products may serve as the sole source of nutrition, they typically don't. Individuals consume these products to replace one or two meals a day, or to provide a healthy snack. The nutritional products of this invention should be construed to include any of these embodiments.

The amount of these nutritional ingredients can vary widely depending upon the targeted patient population (i.e. diabetics vs. non-diabetics, organoleptic considerations, cultural preferences, age, use, etc.). Although not intended to limit the invention in any manner, but to merely serve as a general guideline, the nutritional formulas of this invention will typically provide the following caloric distribution. The protein system will typically provide from about 10% to about 35% of total calories, more preferably from about 15% to about 25% of total calories. The lipid system will provide less than about 37% of total calories, more preferably about 10% to about 30% of total calories. The carbohydrate system will typically provide from about 25% to about 75% of total calories, more preferably from about 35% to about 70% of total calories.

The novelty of these meal replacement products is the successful incorporation of the induced viscosity fiber system that generates an acid induced viscous digesta.

The first component of the meal replacement products of the instant invention is carbohydrate. The soluble fiber of the induced viscosity fiber system is considered part of the carbohydrate system. Numerous types of dietary fibers are known and available to one practicing the art. Fibers differ significantly in their chemical composition and physical structure and therefore their physiological functions. The dietary fiber sources utilized in this invention can be characterized by the term solubility. Fiber can be divided into soluble and insoluble types and fiber sources differ in the amount of soluble and insoluble fiber they contain.

Representative of soluble dietary fiber sources are gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low and high methoxy pectin, β-glucans, carrageenan and psyllium. Numerous commercial sources of soluble dietary fibers are readily available and known to one practicing the art. For example, gum arabic, hydrolyzed carboxymethylcellulose, guar gum, xanthan gum, alginates, pectin and the low and high methoxy pectins are available from TIC Gums, Inc. of Belcamp, Md. The oat and barley glucans are available from Mountain Lake Specialty Ingredients, Inc. of Omaha, Nebr. Psyllium is available from the Meer Corporation of North Bergen, N.J. while the carrageenan and konjac flour are available from FMC Corporation of Philadelphia, Pa.

Preferably, the soluble fibers of the instant invention are also anionic. Representative of anionic soluble dietary fiber sources are alginate, pectin, low methoxy pectin, carrageenan, xanthan and gellan gum.

Practitioners typically refer to the total amount (or percentage) of fiber in a serving. The amount of soluble anionic fiber required for the induced viscosity fiber system is from about 0.4 w/w % to 3.0 w/w % of the meal replacement product, preferably from about 1.0 w/w % to 3.0 w/w % of the meal replacement product, more preferably from about 2.0 w/w % to about 3.0w/w % of the meal replacement product. A single meal replacement serving is typically about 250 gm.

Any single anionic fiber listed above, or any combination thereof may be utilized in the induced viscosity fiber system of the instant invention. The preferred anionic soluble fiber source is alginate because it is less viscous and less fermentable than other soluble fibers. Alginate is the salt of alginic acid and is isolated from brown seaweed, family Phaeophyceae. It is composed of mannuronic (pKa~3.38) and guluronic acid (pKa~3.65). Alginate, in the absence of free polyvalent cations, is a relatively nonviscous soluble fiber. Alginate solutions gel upon addition of free calcium ions, which fill the cavities formed between parallel guluronic acid chains. These cavities contain two carboxylate and two hydroxyl groups, one from each chain.

The remaining portion of the carbohydrate system may be provided by any carbohydrate system suitable for humans, taking into account any relevant dietary restrictions (i.e. if intended for a diabetic). As indicated above, the carbohydrate typically contributes from about 25% to about 75% of total calories. Examples of suitable carbohydrates that may be utilized include maltodextrin, glucose polymers, sucrose, maltitol, honey, sugar alcohols, corn syrup solids, glucose, fructose, lactose, and high fructose corn syrup.

In addition to the carbohydrates described above, the nutritionals may also contain indigestible oligosaccharides such as fructooligosaccharides (FOS). Indigestible oligosaccharides are rapidly and extensively fermented to short chain fatty acids by anaerobic microorganisms that inhabit the large bowel. These oligosaccharides are preferential energy sources for most *Bifidobacterium* species, but are not utilized by potentially pathogenic organisms such as *Clostridium perfingens, C. difficile*, or *E. coli*. The term "indigestible oligosaccharide" refers to a small carbohydrate moiety with a degree of polymerization less than or equal to about 20 and/or a molecular weight less than or equal to about 3,600, that is resistant to endogenous digestion in the human upper digestive tract.

Figure 3:
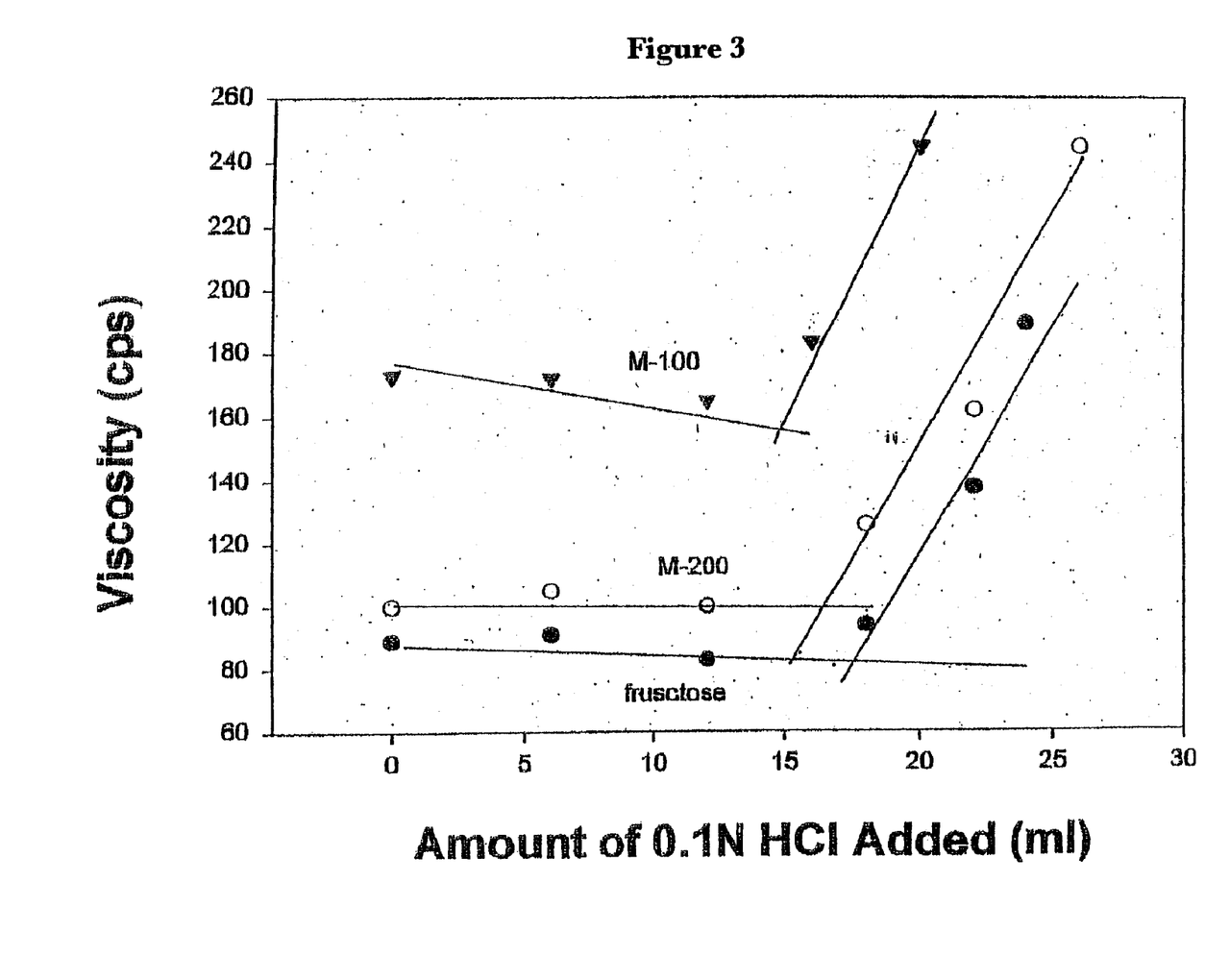
FIG. 3: Effect of Carbohydrate Source on Acid Requirements

One skilled in the art is aware that the carbohydrates selected to fill the remaining portion of the carbohydrate system will affect the initial ready-to-feed viscosity of the nutritional product. For example, in Example 3, less hydrolyzed starches (i.e. DE 10 vs DE 20) will increase the ready-to-feed viscosity.

The preferred carbohydrate system typically comprises 10 wt/wt % alginate, 23 wt/wt % fructose, 20 wt/wt % maltitol, 4 w/w % FOS and 43 wt/wt % maltodextrin DE10.

The meal replacement products also typically contain a protein source. The proteins that may be utilized in the nutritional products of the invention include any proteins suitable for human consumption. Such proteins are well known by those skilled in the art and can be readily selected when preparing such products. Examples of suitable proteins that may be utilized typically include casein, whey, milk protein, soy, pea, rice, corn, hydrolyzed protein, mineral enriched proteins and mixtures thereof. Commercial protein sources are readily available and known to one practicing the art. For example, caseinates, whey, hydrolyzed caseinates, hydrolyzed whey and milk proteins are available from New Zealand Milk Products of Santa Rosa, Calif. Soy and hydrolyzed soy proteins are available from Protein Technologies International of Saint Louis, Mo. Pea protein is available from Feinkost Ingredients Company of Lodi, Ohio. Rice protein is available from California Natural Products of Lathrop, Calif. Corn protein is available from EnerGenetics Inc. of Keokuk, Iowa.

When selecting an appropriate protein source, one skilled in the art is aware that native protein can trap the soluble fiber in globules preventing it from cross-linking with the ionized salts. Additionally, protein can carry carboxy groups that will compete with the soluble fiber for the ionized calcium resulting in an increase in the acid requirement.

Figure 1:
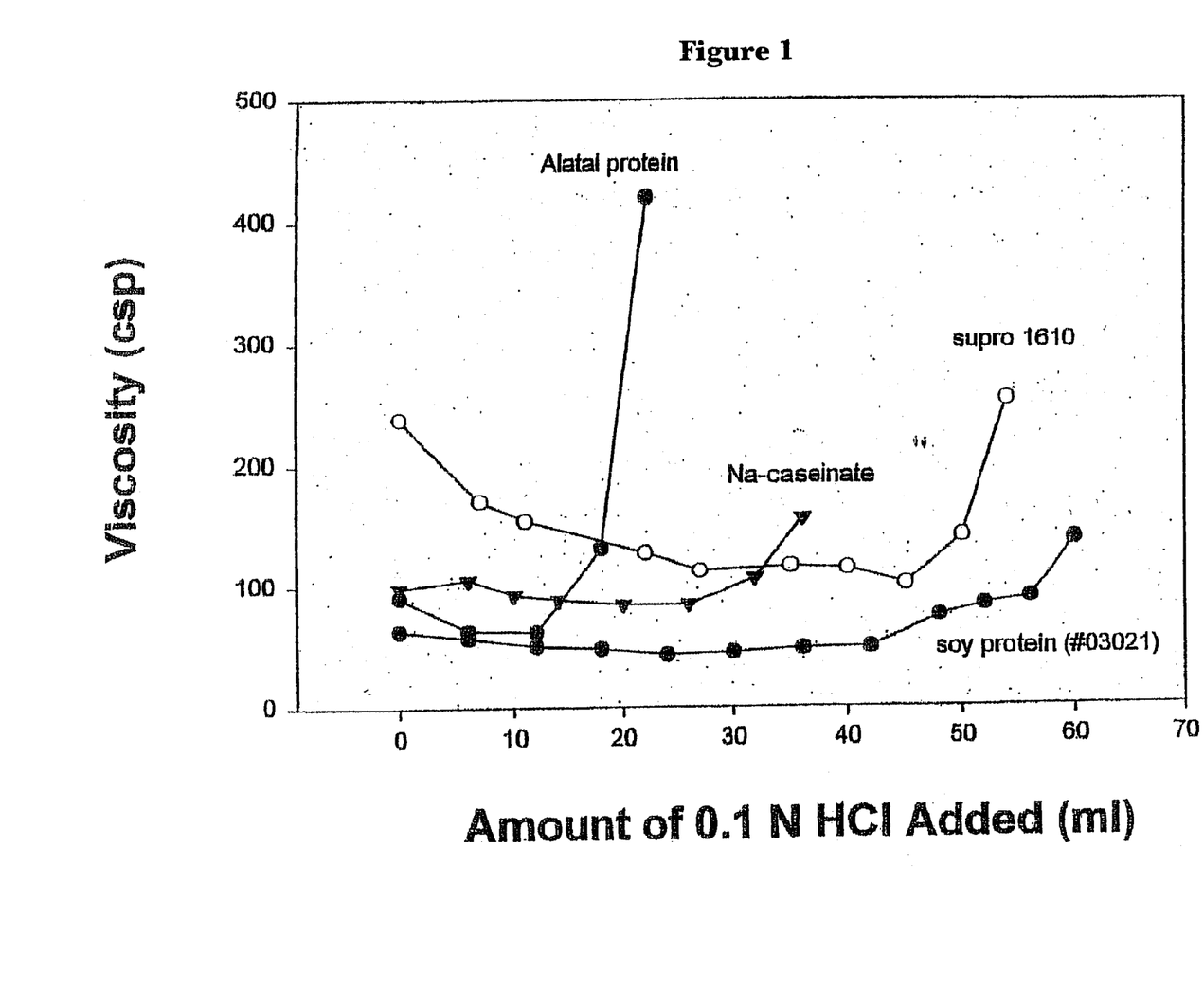
FIG. 1: Effect of Protein Source on Acid Requirement

The Experiments below demonstrate that the protein system selection can influence the acid requirement and the rate of viscosity development. For example, as described in Experiment 1, some proteins such as calcium caseinate and milk protein isolate react with alginate, which negatively impacts the in vivo induced viscosity. Other proteins, such as soy protein, compete with alginate for the free calcium, which negatively impacts the in vivo induced viscosity.

The preferred protein system typically comprises about 47 w/w % heat denatured whey protein, about 29 w/w % whey protein isolate and about 24 w/w % sodium caseinate.

The third component of the nutritional products of this invention is the fat. The fat source for the present invention may be any fat source or blend of fat sources suitable for human consumption. As noted above, the fat source of this invention will typically provide less than or equal to 37% of the total calories. The fat source for the present invention may be any fat source or blend of fat sources which provides the desired levels of saturated (less than 10% kcal), polyunsaturated (up to 10% kcal) and monounsaturated fatty acids (10% to 15% kcal). One skilled in the art can readily calculate how much of a fat source should be added to the nutritional product in order to deliver the desired levels of saturated, polyunsaturated and monounsaturated fatty acids. Examples of food grade fats are well known in the art and typically include soy oil, olive oil, marine oil, sunflower oil, high oleic sunflower oil, safflower oil, high oleic safflower oil, fractionated coconut oil, cottonseed oil, corn oil, canola oil, palm oil, palm kernel oil and mixtures thereof.

Numerous commercial sources for the fats listed above are readily available and known to one practicing the art. For example, soy and canola oils are available from Archer Daniels Midland of Decatur, Ill. Corn, coconut, palm and palm kernel oils are available from Premier Edible Oils Corporation of Portland, Oreg. Fractionated coconut oil is available from Henkel Corporation of LaGrange, Ill. High oleic safflower and high oleic sunflower oils are available from SVO Specialty Products of Eastlake, Ohio. Marine oil is available from Mochida International of Tokyo, Japan. Olive oil is available from Anglia Oils of North Humberside, United Kingdom. Sunflower and cottonseed oils are available from Cargil of Minneapolis, Minn. Safflower oil is available from California Oils Corporation of Richmond, Calif.

The nutritional compositions of the invention desirably contain vitamins and minerals. Vitamins and minerals are understood to be essential in the daily diet. Those skilled in the art appreciate that minimum requirements have been established for certain vitamins and minerals that are known to be necessary for normal physiological function. Practitioners also understand that appropriate additional amounts of vitamin and mineral ingredients need to be provided to nutritional compositions to compensate for some loss during processing and storage of such compositions. Additionally, the practitioner understands that certain micronutrients may have potential benefit for people with diabetes such as chromium, carnitine, taurine and vitamin E and that higher dietary requirements may exist for certain micro nutrients such as ascorbic acid due to higher turnover in people with diabetes.

The second component of the induced viscosity fiber system is water-insoluble multivalent cations that are ionized under acidic conditions.

Representative of water-insoluble multivalent cation sources that are acid-soluble are magnesium, calcium, iron, chromium, manganese, molybdenum, copper, zinc, calcium carbonate, calcium fluoride, calcium molybdate, calcium oxalate, calcium phosphate dibasic, calcium phosphate tribasic, calcium pyrophosphate, calcium saccharate, magnesium fluoride, magnesium hydroxide, magnesium oxide, magnesium peroxide, magnesium phosphate tribasic, magnesium pyrophosphate, magnesium selenite, manganese carbonate, manganese oxide, manganese sulfide and combinations thereof. Numerous commercial sources water-insoluble, acid-soluble multivalent cation sources are readily available and known to one practicing the art. For example, tricalcium phosphate is available from Fortitech in Schenectady, N.Y. Calcium carbonate is available from Specialty Minerals Inc. in Bethlehem, Pa. Magnesium phosphate is available from Jost Chemicals in St. Louis, Mo. Calcium phosphate monobasic is available from Monsanto Company in St. Louis, Mo.

Figure 2:
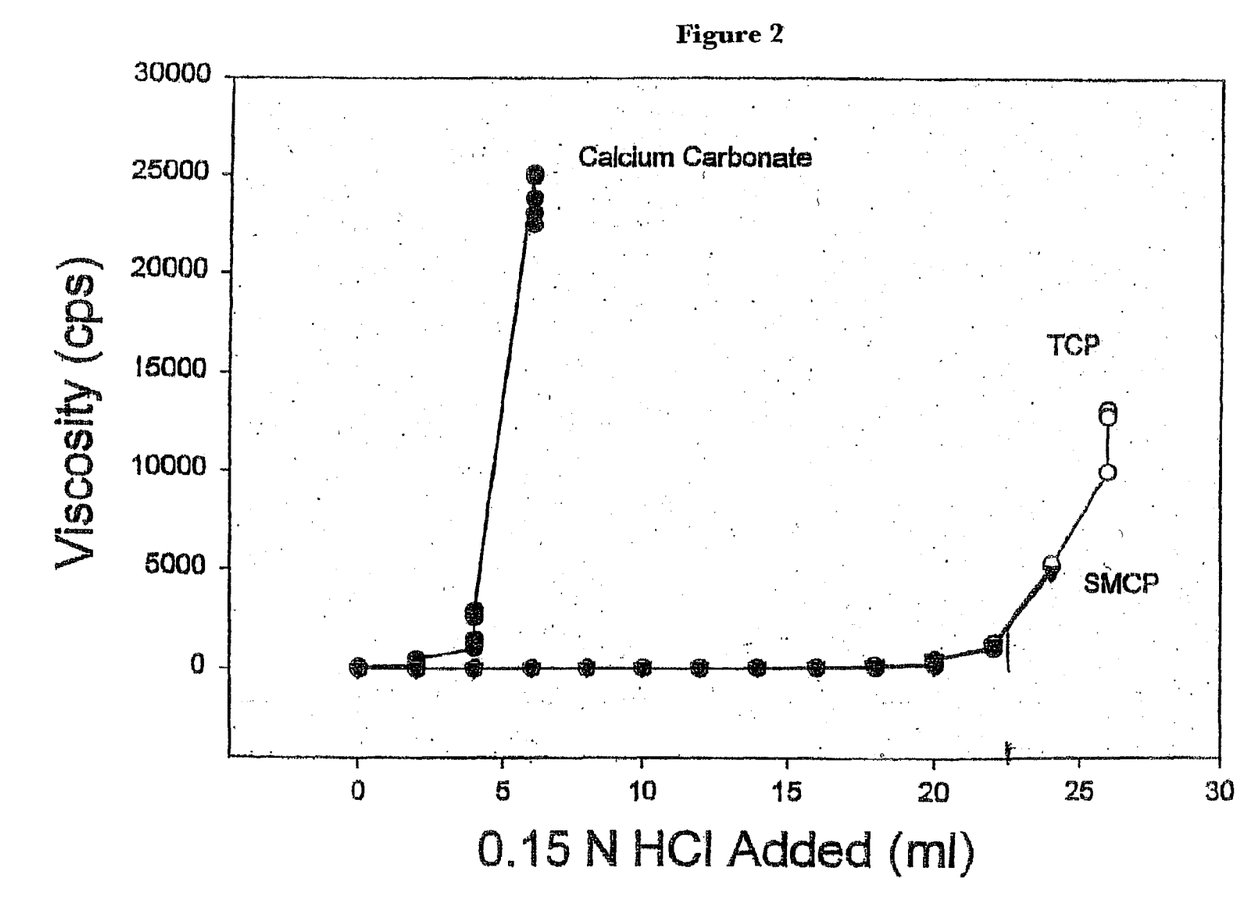
FIG. 2: Effect of Salt Source on Acid Requirement

Experiment 2 describes how different multivalent cations effect the acid requirement of a model fiber system. Calcium carbonate had a significantly lower acid requirement than the tricalcium phosphate (TCP) or the self-manufactured calcium phosphate (SMCP).

Any single multivalent cation listed above, or any combination thereof may be utilized in the induced viscosity fiber system of the instant invention. The preferred multivalent cation source is calcium carbonate. Typically amounts of multivalent cations required to cross-link with the soluble anionic fiber is from about 200 ppm to about 9000 ppm, preferably from about 200 ppm to about 4000 ppm, more preferably from about 300 ppm to 1000 ppm.

Figure 4:
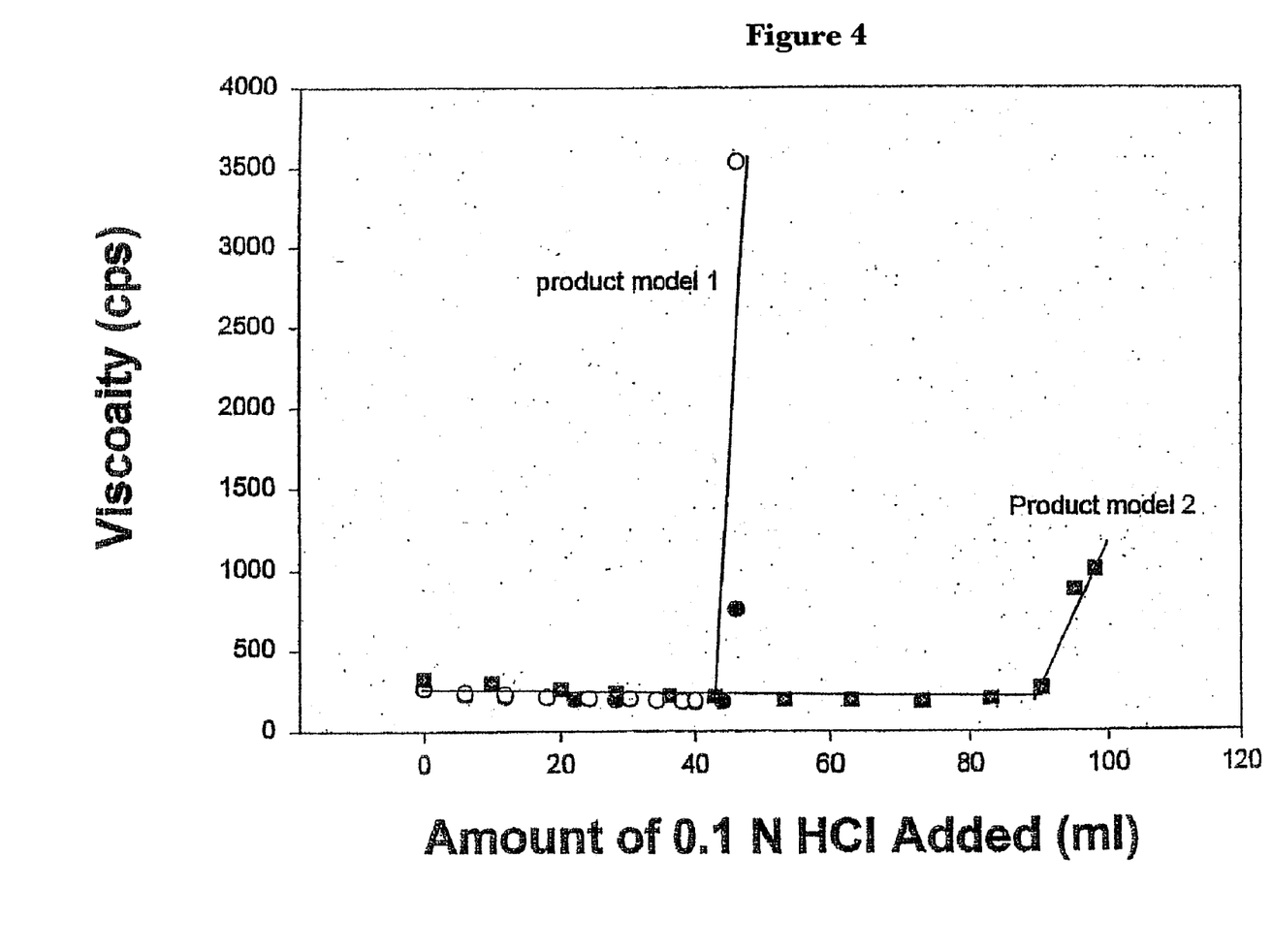
FIG. 4: Effect of Salt Profile on Acid Requirements

As discussed above, the induction of viscosity system depends upon the ionization of free cations to cross-link the soluble anionic fiber molecules. However, other minerals present in the nutritional may negatively impact the induced viscosity. For example, as described in Experiment 4, the acid requirement of the nutritional model was significantly higher than that of a carbohydrate/alginate/tricalcium phosphate mixture. This increase in acid requirement was due to the presence of $MgHPO_4$ and $K_2HPO_4$, which competed with the calcium salts for the added acid. Consequently, minimum levels of basic salts, salts with buffering action and salts with multivalent cations that are, at worst, only sparingly soluble may be included in a nutritional containing the induced viscosity fiber system of the instant invention. Additionally, the induced viscosity system may be "pushed" too far by excess cations to form a rigid gel that is broken down under the shear of the stomach, resulting in a loss of viscosity. Typically multivalent cations are kept below a level of about 15,000 ppm.

An example of the vitamin and mineral system for a nutritional formulation used as a meal replacement typically comprises at least 20% of the RDI for the vitamins A, $B_1$, $B_2$, $B_6$, $B_{12}$, C, D, E, K, beta-carotene, biotin, folic acid, pantothenic acid, niacin, and choline; the minerals calcium, magnesium, potassium, sodium, phosphorous, and chloride; the trace minerals iron, zinc, manganese, copper, and iodine; the ultra trace minerals chromium, molybdenum, selenium; and the conditionally essential nutrients m-inositol, carnitine and taurine in a single serving or from about 50 Kcal to about 1000 Kcal. This level of minerals typically supplies sufficient multivalent cations to support the induced viscosity fiber system.

Artificial sweeteners may also be added to the nutritional formula to enhance the organoleptic quality of the formula. Examples of suitable artificial sweeteners include saccharine, aspartame, acesulfame K and sucralose. The nutritional products of the present invention will also desirably include a flavoring and/or color to provide the nutritional products with an appealing appearance and an acceptable taste for oral consumption. Examples of useful flavorings typically include strawberry, peach, butter pecan, chocolate, banana, raspberry, orange, blueberry and vanilla.

Upon digestion, the induced viscosity fiber system is exposed to acid, which ionizes the multivalent cation that cross-links the anionic soluble fiber increasing the viscosity. The induced viscosity fiber system of the instant invention generates a viscous digesta resulting in the slow release of nutrients into the small intestine. The slow release of nutrients into the small intestine results in prolonged absorption of nutrients, thereby blunting the glycemic response to the meal. The viscosity generated in vivo by the acid controlled induced viscosity fiber system is greater than about 300 cps, preferably at least about 1000 cps, more preferably at least 3000 cps.

The induced viscosity fiber system has been designed to generate optimal viscosity in vivo while minimizing the ready-to-feed viscosity. As discussed previously, when compared to other soluble fibers, the preferred anionic soluble fibers typically generate lower viscosity in solution, thereby producing an acceptable drinkable product The ready-to-feed viscosity of the acid controlled induced viscosity fiber system is less than about 300 cps, preferably less than about 200 cps, more preferably from about 50 cps to about 150 cps.

Preferably, the induced viscosity fiber system is formulated to produce maximum viscosity with minimum acid requirement. The induced viscosity fiber system is formulated to require less than about 120 ml of acid per 250 gm of product, preferable less than about 60 ml of acid per 250 gm product.

The nutritional products of this invention can be manufactured using techniques well known to those skilled in the art. While manufacturing variations are certainly well known to those skilled in the nutritional formulation arts, a few of the manufacturing techniques are described in detail in the Examples. Generally speaking a fiber in oil blend is prepared containing all oils, soluble fiber, any emulsifier, stabilizer and the fat soluble vitamins. Two more slurries (protein and carbohydrate) are prepared separately. The carbohydrate and minerals are mixed together and the protein is mixed in water. The protein in water and carbohydrate/mineral slurries are then mixed together with the oil blend. The resulting mixture is homogenized, heat processed, standardized with water soluble vitamins, and flavor. The final blend is homogenized and aseptically filled in to appropriate containers. Alternatively, the homogenized formula may be kept undiluted and dried to form powder. The product is then packaged. Typically the package will provide directions for use by the end consumer (i.e. to be consumed by a diabetic, to assist with weight loss, etc.).

A second embodiment of the instant invention is a method of blunting the postprandial glycemic response in a human by feeding the induced viscosity fiber system described above. The inventors discovered, in Experiment 5, that the acid controlled induced viscosity fiber system improved the glycemic response without decreasing insulin response in healthy non-diabetic humans.

A third embodiment of the instant invention is a method of promoting the feeling of fullness in a human by feeding the induced viscosity fiber system described above. The inventors discovered, in Experiment 6, that nutritional products containing the induced viscosity fiber system would delay gastric emptying thereby increasing the feeling of fullness.

The embodiments of the present invention may, of course, be carried out in other ways than those set forth herein without departing from the spirit and scope of the invention. The present embodiments are, therefore, to be considered in all respects as illustrative and not restrictive and that all changes and equivalents also come within the description of the present invention. The following non-limiting Examples will further illustrate the present invention.

Experiment 1

Initial experimentation evaluated the effect different protein sources had on the acid requirement of the induced viscosity system.

Alginate stock solutions were prepared by adding 1% of low viscosity sodium alginate (Kelton LVCR from Kelco Company in San Diego, Calif.) to water under vigorous agitation. The alginate stock solution was then allowed to rest for 4 hours before use. Sixteen grams of various protein sources was slowly added to 184 g of water under agitation and the pH of the protein solution was adjusted to 6.8 before 0.2% of tricalcium phosphate(TCP) and 200 g of alginate solution was added. The mixture was titrated with 0.1N HCl and the viscosity of the model systems were measured using the Brookfield (model DVII+) viscometer with a 62 spindle at room temperature The inventors had previously shown that calcium caseinate and milk protein isolate react with alginate and were less suitable for this application. Likewise, soluble whey proteins (native globular protein) had been found less suitable for this application, because, when used as the sole source of protein, whey was found to trap the alginate and render the induced viscosity system nonfunctional after processing. Consequently, these protein sources were not included in this study.

FIG. 1 shows the effect denatured whey protein (Alatal from New Zealand Milk Products in Santa Rosa, Calif.), sodium caseinate, and two soy protein sources (Supro 1610 from PTI in St. Louis, Mo.) had on the acid requirement of the induced viscosity system. While the soy proteins and sodium caseinate protein required significantly more acid before an increase in viscosity was measured, the whey protein required less acid and achieved a significant viscosity. Soy protein, while not very soluble, was very effective in competing with alginate for the free calcium and was less suitable for this application. The heat denatured whey protein was the most suitable protein source for the acid controlled induced viscosity system. The heat denatured whey protein was the most functional protein for this application because it has a lower level of glutamic/aspartic acid compared with soy protein and a lower level of phosphoserine compared with the caseinate protein.

Experiment 2

Initial experimentation evaluated the effect different calcium sources had on the acid requirement of the induced viscosity system.

Solutions containing various calcium salts (0.1% tricalcium phosphate (TCP), calcium carbonate ($CaCO_3$) or self-manufactured calcium phosphate (SMCP), 4% whey protein (Alatal 825 from New Zealand Milk Products in Santa Rosa, Calif.) or high calcium soy protein (from Protein Technologies International in St. Louis, Mo.), 0.5% low viscosity potassium alginate (Kelmar from Kelco Co. in San Diego, Calif.), 0.5% low viscosity sodium alginate (Kelton LVCR from Kelco Co. in San Diego, Calif.), and 0.5% sodium azide (which acts as a preservative) were prepared and their viscosity monitored for 8 weeks. The mixtures containing the high calcium protein gelled in 2 days even in the absence of any added calcium salts. This high calcium soy protein isolate released calcium in the presence of the alginate, thereby inducing the viscosity in the can. Mixtures containing the whey protein (Alatal from New Zealand Milk Products in Santa Rosa, Calif.) plus insoluble calcium salts were stable. The viscosities of these model systems remained unchanged during the 8 week storage study.

The model systems were titrated with acid and, as seen in FIG. 2, the viscosity significantly increased once a threshold level of acid was added. The inventors were surprised to discover that calcium carbonate had a significantly lower acid requirement than the tricalcium phosphate (TCP) and the self-manufactured calcium phosphate (SMCP).

Experiment 3

Initial experimentation evaluated the effect different carbohydrate sources had on the acid requirement of the induced viscosity system.

Forty grams of various types of carbohydrates and 0.4 g of tricalcium phosphate (TCP) was added to 360 g of protein/alginate solution containing 0.5% low viscosity potassium alginate (Kelmar from Kelco Co. in San Diego, Calif.), 0.5% low viscosity sodium alginate (Kelton LVCR from Kelco Co. in San Diego, Calif.), 4% whey protein (Alatal from New Zealand Milk Products in Santa Rosa, Calif.) after the pH of the alginate/protein solution was adjusted to 6.8. The carbohydrates evaluated included maltodextrin DE10 (Maltrin 100 from Grain Processing Corp. in Muscatine, Iowa), corn syrup solids DE20 (Maltrin 200 from Grain Processing Corp. in Muscatine, Iowa) and fructose. The resultant mixtures were titrated with 0.1N HCl acid. As seen in FIG. 3, the type of carbohydrate affected the initial viscosity but produced little impact on the acid requirements.

Experiment 4

Two carbohydrate/mineral model systems were evaluated to determine how the salt profile affected acid requirements.

TABLE 1

Salt and Carbohydrate Factor Sets of Acid Controlled Induced Viscosity Model Systems

| Ingredient | Salts factor sets of Product Model 1 (gm/gm) | Salts factor sets of Product Model 2 (gm/gm) |
|---|---|---|
| $K_2HPO_4$ | 0.00150 | 0.0013 |
| $CaCO_3$ | 0.00030 | 0 |
| KCl | 0.00115 | 0.00082 |
| Tricalcium phosphate | 0.0036 | 0.0038 |
| $MgHPO_4$ | 0.00315 | 0.003 |
| UTM/TM premix* | 0.00034 | 0.00034 |
| DE 1 Maltodextrin | 0.084 | 0.084 |
| NaCl | 0.0004 | 0.00068 |

*Per gm of UTM/TM premix: 83 mg zinc, 65 mg iron, 18 mg manganese, 7.8 mg copper, 0.262 mg selenium, 0.365 mg chromium, 0.585 molybdenum.

The initial viscosity of these systems were substantially higher than the Alatal/Alginate/carbohydrate mixtures which may be due to the higher molecular weight maltodextrin used in the model study. Inclusion of 0.03% $CaCO_3$ (Model 1) significantly reduced the acid requirement (FIG. 4). Further increasing the $CaCO_3$ level did not further reduce the acid requirement but produced a significant increase in the initial viscosity.

The acid requirement of the model is significantly higher than that of a carbohydrate/alginate/TCP mixture. Presumably, this increase in acid requirement is due to the presence of $MgHPO_4$ and $K_2HPO_4$, which may compete with the calcium salts for the added acid.

The model suggested that a complete acid controlled induced viscosity product may be manufactured using heat denatured whey as the protein source, $CaCO_3$ as the calcium trigger, and minimum levels of basic salts and/or salts with divalent cations that are, at worst, only sparingly soluble.

EXAMPLE I

The manufacture of 454 kg of a nutritional product that contains the acid controlled induced viscosity fiber system of the instant invention is described below. The required amounts of ingredients (Table 2) for the fiber in fat slurry were combined and held.

TABLE 2

Fiber in Fat Slurry

| High oleic safflower oil | 8.17 kg |
| Canola oil | 0.96 kg |
| Soy lecithin | 0.47 kg |
| Vitamin DEK premix* | 30.87 gm |
| Beta carotene 30% | 3.63 gm |
| Vitamin A palmitate | 3.41 gm |
| Sodium alginate | 3.3 kg |
| Potassium alginate | 0.8 kg |

*per gm Vitamin DEK premix: 8130 IU vitamin $D_3$, 838 IU vitamin E, 1.42 mg vitamin $K_1$.

The required amount of ingredients (Table 3) for the protein in water slurry were combined and held.

TABLE 3

Protein in Water Slurry

| Water | 173 kg |
| Alatal | 17.4 kg |

The required amount of ingredients (Table 4) for the carbohydrate/mineral slurry were combined and held.

TABLE 4

Carbohydrate/Mineral Slurry

| Water | 54.6 kg |
| Maltrin 200 | 25 kg |
| Sucrose | 6.8 kg |
| Fructose | 6.8 kg |
| Tricalcium phosphate | 1.8 kg |
| Magnesium phosphate dibasic | 1.8 kg |
| Magnesium chloride | 363 gm |
| Potassium chloride | 317 gm |
| UTM/TM premix* | 204 gm |
| Calcium carbonate | 136 gm |
| Sodium chloride | 90 gm |
| Potassium iodide | 0.11 gm |

*Per gm of UTM/TM premix: 83 mg zinc, 65 mg iron, 18 mg manganese, 7.8 mg copper, 0.262 mg selenium, 0.365 mg chromium, 0.585 molybdenum.

After each slurry was prepared, the carbohydrate/mineral slurry was added to the protein in water slurry. The blend pH was adjusted to 6.6-6.8. The fiber in fat slurry was then added to the blend. The blend was processed at UHT temperatures (295° F. for 5 seconds) and homogenized at 4000 psi.

The required amount of ingredients (Table 5) for the vitamin solution were combined and the pH was adjusted to 7.0-10.0 using 45% KOH. The pH adjusted solution was held.

TABLE 5

Vitamin Solution

| Water | 13.4 kg |
| Ascorbic acid | 227 gm |
| Choline chloride | 181 gm |
| L-Carnitine | 50 gm |
| WSV premix* | 36 gm |
| Taurine | 45 gm |
| Vanilla flavor | 1.7 kg |

*per gm of WSV premix: 375 mg niacinamide, 242 mg calcium pantothenate, 8.4 mg folic acid, 62 mg thiamine chloride, 48 mg riboflavin, 59 mg pyridoxine hydrochloride, 165 mcg cyanocobalamin, and 7305 mcg biotin.

The vitamin solution was added to the processed blend at standardization. The final blend was UHT heated to 295° F.

for 5 seconds and homogenized at 4000 psi and aseptically filled into sterile 32 oz bottles.

Figure 5:
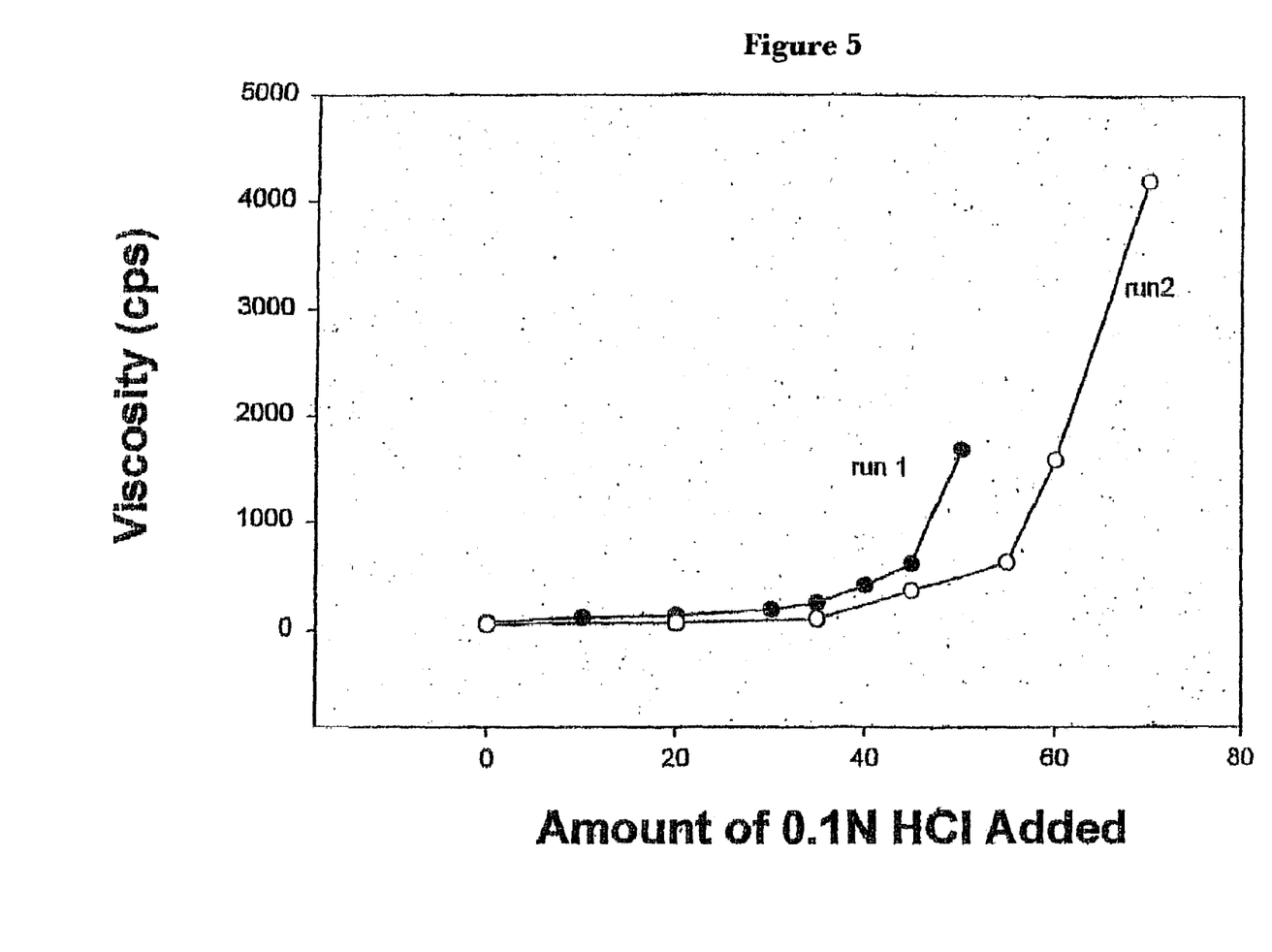
FIG. 5: Responses of the Acid Controlled Induced Viscosity Prototypes to the Addition of 0.1N HCl

The product manufactured as described above had an initial viscosity of 84 cps and developed an induced viscosity of about 3,000 cps upon addition of 50 ml of 0.1N HCl acid. However, a check of the sensory quality of the samples from this manufacturing run found the product to have a gritty mouth feel. The Alatal (insoluble whey protein from New Zealand Milk Products in Santa Rosa, Calif.) was thought to be the cause of the gritty mouth feel (see run 1 in FIG. 5).

EXAMPLE II

Based on the results of Example I, a reduction of the Alatal particle size and a reduction in the level of the heat treated whey protein were factors identified in which to address the gritty mouth feel.

Alatal was replaced with Alacen (spray dried heat denatured whey protein from New Zealand Milk Products in Santa Rosa, Calif.). Alacen has a smaller particle size. Additionally, a low viscosity sodium caseinate was included as 25% of the protein source and a native whey protein was included as 30% of the protein source to reduce the fraction of Alacen. Product was manufactured as the 454 kg of product described above using the protein in water slurry and carbohydrate slurry listed below.

The required amount of ingredients (Table 6) for the protein in water slurry were combined and held.

TABLE 6

Protein in Water Slurry

| Water | 150 kg |
|---|---|
| Sodium caseinate | 4 kg |
| Whey protein isolate | 4.8 kg |
| Alacen | 7.8 kg |

The required amount of ingredients (Table 7) for the carbohydrate/mineral slurry were combined and held.

TABLE 7

Carbohydrate/Mineral Slurry

| Water | 44 kg |
|---|---|
| Maltrin 200 | 25 kg |
| Sucrose | 6.8 kg |
| Fructose | 6.8 kg |
| Tricalcium phosphate | 1.9 kg |
| Magnesium phosphate dibasic | 1.4 kg |
| Potassium chloride | 1.1 kg |
| Magnesium chloride | 363 gm |
| UTM/TM Premix* | 204 gm |
| Calacium carbonate | 136 gm |
| Sodium chloride | 90 gm |
| Potassium iodide | 50 gm |

*Per gm of UTM/TM premix: 83 mg zinc, 65 mg iron, 18 mg manganese, 7.8 mg copper, 0.262 mg selenium, 0.365 mg chromium, 0.585 molybdenum.

The mouth feel of the product was significantly improved with the addition of the modified protein system. The viscosity of the product manufactured above was 65 cps. When treated with 70 ml of 0.1N HCl, 250 g of the acid controlled induced viscosity sample developed a viscosity of 4,200 cps (see run 2 in FIG. 5).

Experiment 5

The present experiment evaluated the clinical efficacy of an acid induced viscosity fiber system (IV) in a glucose-based product matrix. The primary objective of this study was to assess the ability of the induced viscosity fiber system to attenuate the postprandial serum glucose and insulin responses in nondiabetic healthy adults.

The acid induced viscosity fiber system was incorporated into a glucose-based beverage and compared to a control glucose-based beverage that had a similar total dietary fiber (TDF) level and initial viscosity. The ingredient composition of the experimental treatments are described in Table 8.

TABLE 8

Ingredient Composition of Experimental Treatments[a]

| | treatment | |
|---|---|---|
| ingredient | Control (gm/100 gm) | IV (gm/100 gm) |
| water | 66.6 | 66.6 |
| glucose | 30 | 30 |
| sodium alginate | 0.0 | 1.5 |
| gum arabic | 1.2 | 0.0 |
| guar gum | 0.3 | 0.0 |
| potassium citrate | 1.2 | 1.2 |
| microcrystalline cellulose | 0.2 | 0.2 |
| tricalcium phosphate | 0.15 | 0.15 |
| flavor, lemon | 0.2 | 0.2 |

[a]Product fill weights were 250 g

Ingredients were made into 31% solutions with water, filled into 250-mL glass bottles, and terminally sterilized (Ross Products Division of Abbott Laboratories, Columbus, Ohio). Experimental products were supplied as a liquid 250 gm single serving.

Chemical composition of experimental treatments was determined in order to verify level of ingredient addition. Total solids were determined according to Association of Official Analytical Chemists methods (AOAC, 1984). Mineral composition was determined by an Inductively Coupled Plasma spectrometry method (Ross Products Division). Monosaccharides were quantified by an ion chromatographic method utilizing a Dionex DX-300 chromatograph fitted with a PA1 CarboPac column (Dionex, Sunnyvale, Calif.) as described by Hogarth et al. (2000). Total dietary fiber was determined using the method of Prosky et al. (1984). Product viscosity was measured utilizing a rotational-type viscometer (Brookfield model DV-II+, #3 spindle at 60 rpm; Brookfield Instruments, Stoughton, Mass.) at 23° C.

A total of 30 healthy nondiabetic adult subjects (19 females and 11 males) were recruited. Subjects had a mean (±SE) age of 36±2 y, weight of 66±2 kg and body mass index between 21 and 28 (24.2±0.4 kg/m$^2$). None of the subjects were taking medication, had a family history of diabetes (first degree relatives), or suffered from a gastrointestinal disorder. Utilizing standard procedures, a complete medical exam (i.e., serum chemistry, hematology, urinalysis, physical exam, and medical history) was performed to document the subject's health prior to enrollment into the study.

The experiment was conducted as a double-masked cross-over study, and experimental products were tested as an oral glucose tolerance test. To ensure that subjects had similar glycogen stores on the two test days, subjects were instructed to consume a high-carbohydrate diet (minimum 200 gm/day) for 3 d before each meal tolerance test and also were asked to avoid exercise 24 h before the experiment. Subjects completed dietary histories for the 3 d before each test in order to estimate carbohydrate intake. Subjects fasted overnight (at least 12 h) prior to each test, during which they were allowed to consume only water. Smoking was prohibited. Subjects returned within 12 d (mean 7±0.3 d, range 4 to 12 d) for repeat analysis with the appropriate crossover treatment. Subjects were allowed water (250 mL) during each 3-h test.

After the overnight fast, an indwelling catheter was placed in a peripheral vein. Subjects were allowed to relax for 30 min, and a baseline blood sample was taken. Subjects then consumed the appropriate product within 10 min, and additional blood samples were taken at 15, 30, 60, 90, 120, 150, and 180 min postprandial. Serum lucose was measured by the glucose oxidase method using the Beckman Glucose Analyzer II (Beckman Instruments, Fullerton, Calif.), and serum immunoreactive insulin was analyzed by Corning Clinical Laboratories (Irving, Tex.).

Using a questionnaire, subjects were asked to report the severity of the following symptoms: nausea, cramping, distention, vomiting, burping, and reflux following each oral glucose tolerance test. Severity was set to the following scale: 0=absent, 1=mild, 2=moderate, 3=severe.

The primary variable for the study was incremental (i.e., baseline-adjusted) peak serum glucose response. Secondary variables for this study were: incremental peak serum insulin response, net incremental area under the curve (AUC) for serum glucose and insulin, relative glycemic response, mean incremental change from baseline in serum glucose and insulin at 15, 30, 60, 90, 120, 150, and 180 min postprandial, and subjective gastrointestinal tolerance factors.

Results

The chemical composition of dietary treatments is presented in Table 9 below.

TABLE 9

Chemical Composition of Experimental Treatments

| item | treatment | |
|---|---|---|
| | Control (units/100 gm product) | IV (units/100 gm product) |
| total solids, g | 31.5 | 30.8 |
| potassium, mg | 466 | 462 |
| calcium, mg | 67.4 | 60.8 |
| phosphorus, mg | 27.6 | 27.7 |
| total dietary fiber, g | 1.88 | 1.77 |
| glucose, g | 24.5 | 24.7 |
| fructose, g[a] | 4.8 | 4.7 |
| galactose, [a] | 0.2 | 0.2 |
| viscosity, mPa · sec | 289 | 249 |

[a]Fructose and galactose were formed during heat processing from the isomerization of glucose.

Dietary treatments were formulated to deliver 75 gm glucose for the oral glucose tolerance test. However, isomerization of glucose occurred during the heat processing (sterilization) of both products. Based upon product analysis, ~61 gm glucose (12 gm fructose and 0.5 gm galactose) was present in each 250 gm serving. It was decided that a 61 gm glucose challenge was acceptable because 50-g carbohydrate loads are typically used in studies of glycemic response. Total dietary fiber composition was similar for the Control and IV treatments (4.7 and 4.4 gm TDF per serving, respectively). In addition, initial product viscosity was similar for the Control and IV treatments (289 and 249 mPa•sec, respectively). The baseline serum glucose value did not differ (P>0.10) between groups (82.6±1.3 and 84.6±1.5 mg/dL for Control and IV, respectively).

Table 10 presents data for mean peak incremental change from baseline and net incremental AUC for serum glucose and insulin. Baseline values for serum glucose were 82.6±1.3 and 84.6±1.5 mg/dL for Control and IV, respectively. Baseline values for serum insulin were 5.2±0.8 and 5.4±0.8 mIU/L for Control and IV, respectively.

TABLE 10

Glycemic and Insulinemic Responses of Healthy Nondiabetic Subjects to an Experimental Acid Induced-Viscosity (I-V) Complex

| Item | glucose (mg/dL) | | insulin (mIU/L) | |
|---|---|---|---|---|
| | Control | IV | Control | IV |
| peak value[a] | 40.4 ± 3.3 | 32.8 ± 3.4[c] | 32.6 ± 3.7 | 59.8 ± 11.9[e] |
| AUC (unit · min)[b] | 1717 ± 433 | 429 ± 276[d] | 2723 ± 326 | 3366 ± 560 |

To convert glucose mg/dL to mmol/L, multiply mg/dL by 0.0555. Glucose of 90 mg/dL = 5.0 mmol/L.
[a]Mean peak serum insulin values represent period one data only
[b]Net incremental area under the curve 180 min postprandial.
[c]IV different from Control (P < 0.06),
[d]IV different from Control (P < 0.01),
[e]IV different from Control (P < 0.05)

Figure 6:
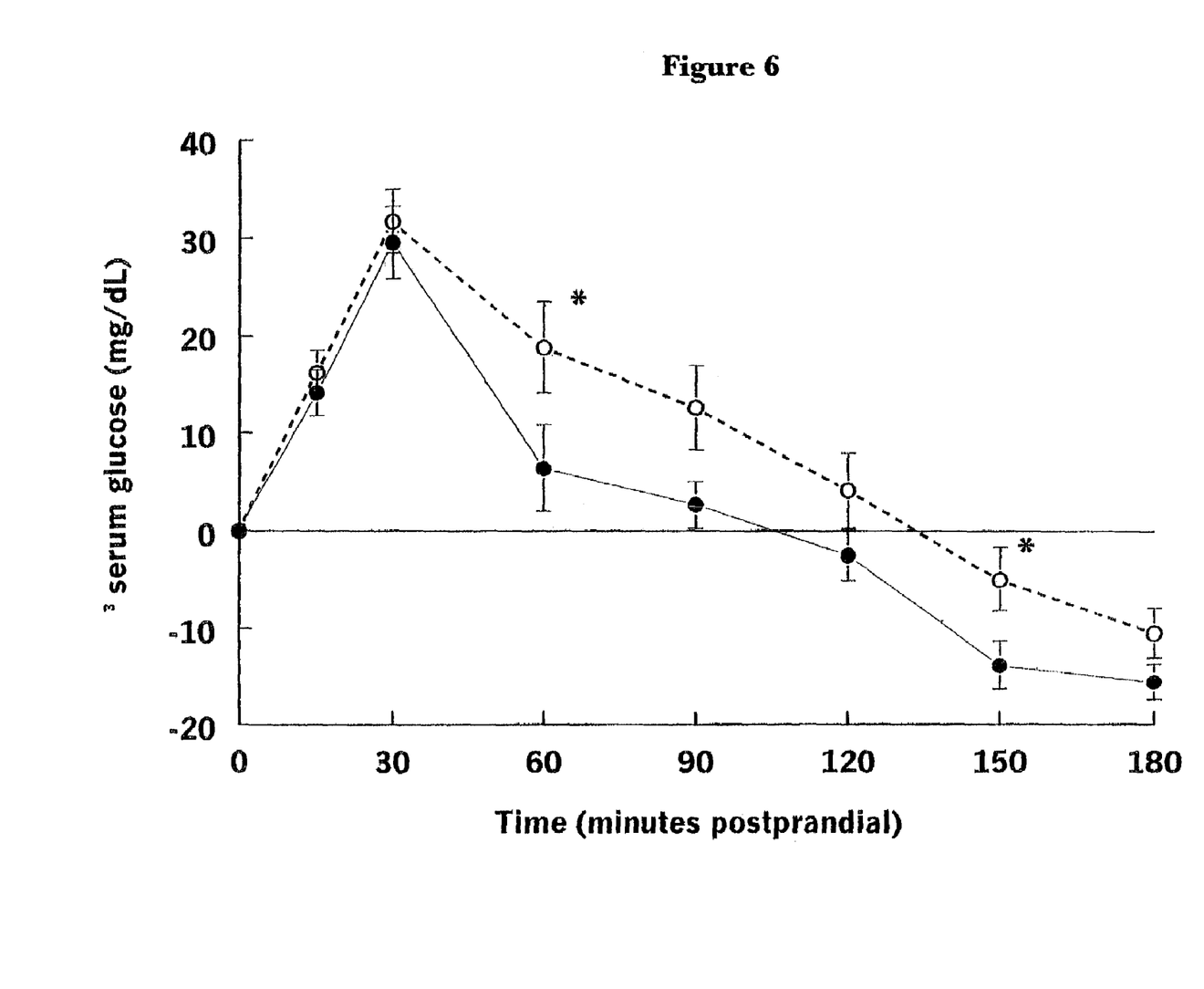
FIG. 6: Incremental change from baseline in serum glucose after ingestion of a glucose beverage (Control-o-) and a glucose beverage containing an experimental acid-induced-viscosity complex (IV-●-) by healthy nondiabetic adult subjects.

There was a trend (P<0.06) toward a reduced mean peak incremental change in serum glucose for the IV product. In addition, the net incremental AUC was lower (P<0.01) for the IV product. The relative glycemic response over the 180-min test was calculated to be 23.3±84.9, whereas the glycemic index over the 180-min test was calculated to be 91.2±14.7. Postprandial glycemic response to the glucose challenge is graphically depicted in FIG. 6. Data are presented as the incremental change from baseline. The postprandial change in serum glucose was not different (P>0.20) between the two products at 15 and 30 min. However, there was a trend toward the blunting of glycemia at 60, 90, and 150 min postprandial for the IV product (P<0.05, P=0.06, and P<0.05, respectively). Serum glucose fell below baseline values at about 120 min postprandial for both products. Time to peak glucose did not differ between products.

Figure 7:
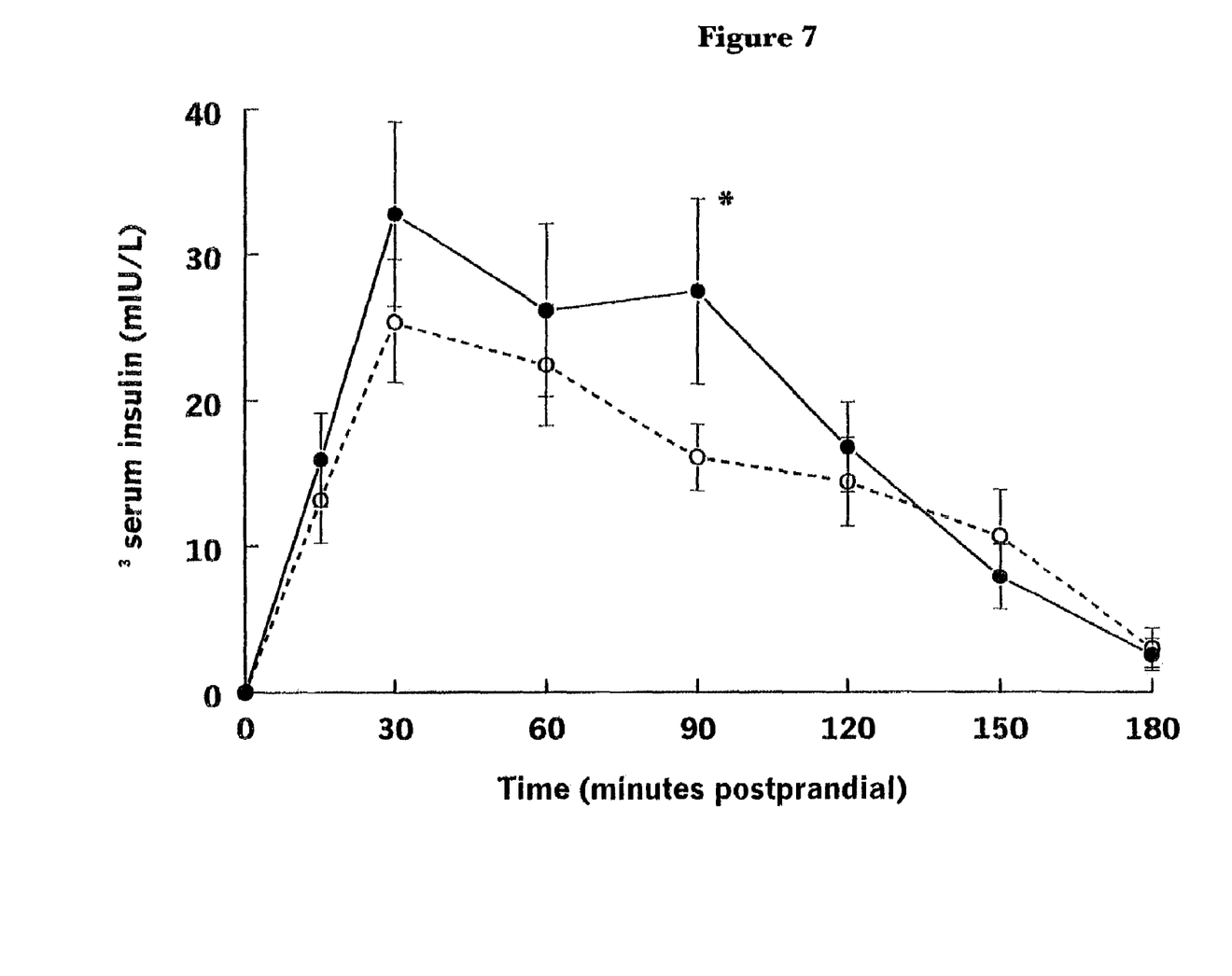
FIG. 7: Incremental change from baseline in serum insulin after ingestion of a glucose beverage (Control-o-) and a glucose beverage containing an experimental acid-induced-viscosity complex (IV-●-) by healthy nondiabetic adult subjects.

The mean peak incremental change from baseline in serum insulin was higher (P<0.05) for the IV product (FIG. 7). Net incremental AUC for serum insulin over the 180-min test did not differ (P>0.20) between products. Postprandial serum insulin responses are depicted in FIG. 7. The baseline serum insulin value did not differ (P>0.20) between groups (5.2±0.8 and 5.4±0.8 mIU/L for Control and IV, respectively). Incremental change from baseline for insulin did not differ (P>0.10) across all time points except at 90 min postprandial in which the Control product had a lower (P<0.01) insulin response. Time to peak for insulin did not differ between products.

Gastrointestinal symptoms were minimally affected by the products fed in this glucose tolerance test. No differences were noted between products. The most frequently reported symptoms were burping and nausea, most of which were mild in nature. No adverse events were documented for subjects consuming either product.

CONCLUSION

The inventors found that the IV formula reduced serum glucose at 60, 90, and 150 min postprandial. Subjects had a higher incremental peak insulin response after consuming the IV product compared to the Control.

No differences in subjective gastrointestinal tolerance symptoms were noted between products in this double-masked experiment. Overall, those symptoms that were reported were scored as mild by the subjects.

In conclusion, the IV complex improved the glycemic response without decreasing insulin response. These data suggest that the IV complex increases insulin secretion relative to the glycemic stimulus.

Experiment 6

The buffering capacity of the experimental treatments described in Experiment 5 was determined in vitro. Incremental levels of simulated gastric fluid were added to 100 g of product and evaluated for changes in pH and viscosity. The inventors found that the viscosity of the IV product did not increase until the pH dropped below 5.0, upon which a sharp rise in viscosity was noted until the pH reached approximately 4. As the pH dropped below 4.0, a large reduction in viscosity was noted. This corroborates well with the pKa of guluronic acid (~3.65). As the pH drops below 4.0, the calcium bridges are broken due to the protonation of the uronic acid groups with hydrogen. Consequently, there is a small pH range upon which the IV complex is efficacious; however, this pH range is achievable under physiological conditions in the stomach. Furthermore, this in vitro study documented the very strong buffering capacity of these products, which have a similar buffering capacity to a standard tube-fed product, Jevity® Plus (Ross Products Division, Columbus, Ohio). It took approximately 50 mL of simulated gastric fluid to bring about the induced-viscosity of 100 gm of product. This suggests that it would require approximately 125 mL of gastric fluid (with 250 gm product) to produce an induced-viscosity complex in vivo. It has been estimated that the healthy adult produces around 100-170 mL of gastric fluid over the first hour postprandial. Thus, not enough acid might have been produced by the subjects in Experiment 5 to induce viscosity at the early time points (15 and 30 min postprandial), and this may explain why differences were only noted at later time points (60, 90, and 150 min postprandial).

Based upon these in vitro results, it appears that the induced-viscosity complex would have its largest impact upon gastric emptying.

We claim:

1. A liquid nutritional composition comprising:
   (A) protein,
   (B) fat,
   (C) from about 0.4% to about 3.0 % by weight of a soluble anionic fiber selected from the group consisting of alginate, low methoxy pectin, carrageenan, xanthan and gellan gum and mixtures thereof, and
   (D) from about 200 ppm to about 9000 ppm of a water-insoluble, acid-soluble, multivalent cation wherein the source of said cation comprises calcium carbonate,
   wherein the composition is a nutritional liquid for use in humans, said composition having an initial viscosity of less than 200 cps and an in vivo viscosity of at least 300 cps.

2. The liquid nutritional composition of claim 1 wherein the soluble anionic fiber represents from about 1.0% to about 3.0% by weight of the composition.

3. The liquid nutritional composition of claim 1 wherein the multivalent cation represents from about 200 ppm to about 1000 ppm by weight of the composition.

4. The liquid nutritional composition of claim 1 wherein the soluble anionic fiber comprises alginate.

5. The liquid nutritional composition of claim 1 wherein the composition comprises from about 200 ppm to about 9000 ppm of calcium carbonate.

6. The liquid nutritional composition of claim 1 wherein the composition comprises protein which represents from about 10 to about 35% of total calories in the composition, fat which represents less than 37% of the total calories, and carbohydrate which represents from about 25% to about 75 % of the total calories.

7. The liquid nutritional composition of claim 1 wherein the composition is a meal replacement beverage.

8. A method for providing nutrition to a diabetic patient comprising feeding to the patient the liquid nutritional composition of claim 1.

9. A method for assisting a diabetic patient with managing their blood glucose levels comprising administering to the patient the liquid nutritional composition of claim 1.

10. A method for producing satiety in a human comprising feeding said human the liquid nutritional composition of claim 1.

11. A method for assisting a human to lose weight comprising feeding said human the liquid nutritional composition of claim 1.

12. A method for blunting the postprandial glycemic response of a diabetic patient comprising administering to the patient the liquid nutritional composition of claim 1.

* * * * *